(12) United States Patent
Egorov et al.

(10) Patent No.: US 10,238,671 B2
(45) Date of Patent: Mar. 26, 2019

(54) HYDROSOLUBLE HYDROXYBISPHOSPHONIC DERIVATIVES OF DOXORUBICIN

(71) Applicant: Atlanthera, Saint-Herblain (FR)

(72) Inventors: Maxim Egorov, Bouguenais (FR);
Jean-Yves Goujon, Derval (FR);
Ronan Le Bot, Nantes (FR);
Emmanuelle David, Port Saint Pere (FR)

(73) Assignee: Atlanthera (FR)

( * ) Notice: Subject to any disclaimer, the term of this patent is extended or adjusted under 35 U.S.C. 154(b) by 0 days.

(21) Appl. No.: 15/528,211

(22) PCT Filed: Nov. 20, 2015

(86) PCT No.: PCT/EP2015/077279
§ 371 (c)(1),
(2) Date: May 19, 2017

(87) PCT Pub. No.: WO2016/079327
PCT Pub. Date: May 26, 2016

(65) Prior Publication Data
US 2017/0319606 A1 Nov. 9, 2017

(30) Foreign Application Priority Data
Nov. 20, 2014 (FR) .................................... 14 61253

(51) Int. Cl.
*A61K 31/663* (2006.01)
*C07F 9/655* (2006.01)
*C07C 335/40* (2006.01)
*C07H 15/244* (2006.01)
*A61K 47/54* (2017.01)

(52) U.S. Cl.
CPC .......... *A61K 31/663* (2013.01); *A61K 47/548* (2017.08); *C07C 335/40* (2013.01); *C07F 9/6552* (2013.01); *C07H 15/244* (2013.01)

(58) Field of Classification Search
CPC .. A61K 31/633; A61K 47/548; C07C 335/40; C07F 9/6552; C07H 15/244
See application file for complete search history.

(56) References Cited

U.S. PATENT DOCUMENTS

| 2010/0311695 A1 | 12/2010 | Egorov et al. |
| 2014/0086843 A1 | 3/2014 | Egorov et al. |

FOREIGN PATENT DOCUMENTS

| WO | 9640156 A1 | 12/1996 |
| WO | 2009083613 A1 | 7/2009 |
| WO | 2009083614 A1 | 7/2009 |
| WO | 2011023367 A2 | 3/2011 |
| WO | 2012130911 A1 | 10/2012 |

OTHER PUBLICATIONS

Hochdorffer, K. et al., "Development of novel bisphosphonate prodrugs of doxorubicin for targeting bone metastases that are cleaved pH dependently or by cathepsin B: synthesis. cleavage properties. and binding properties to hydroxyapatite as well as bone matrix", Journal of Medicinal Chemistry, vol. 55, No. 17, Sep. 2012, pp. 7502-7515.
International Search Report from Application No. PCT/EP2015/077279, dated Apr. 26, 2016.
Kholod et al., "Application of Quantum Chemical Approximations to Environmental Problems: Prediction of Water Solubility for Nitro Compounds", Environmental Science & Technology, vol. 43, No. 24, Dec. 2009, pp. 9208-9215.
Moriceau, et al., "Therapeutic approach of primary bone tumours by bisphosphonates", Current Pharmaceutical Design, vol. 16, Issue 27, Sep. 2010, pp. 2981-2987.
Scozzafava, A. et al., "Carbonic anhydrase inhibitors. A general approach for the preparation of water-soluble sulfonamides incorporating polyamino-polycarboxylate tails and of their metal complexes possessing long-lasting topical intraocular pressure-lowering properties", Journal of Medicinal Chemistry, vol. 45, No. 7, Mar. 2002, pp. 1466-1476.

*Primary Examiner* — Robert H Havlin
(74) *Attorney, Agent, or Firm* — Lerner, David, Littenberg, Krumholz & Mentlik, LLP

(57) ABSTRACT

The invention relates to hydrosoluble hydroxybisphosphonic derivatives of doxorubicin of formula (I) and the pharmaceutically acceptable salts thereof. The invention also relates to the use of said compounds as a drug, especially in the treatment of a bone tumour. The invention further relates to the pharmaceutical compositions comprising such compounds, the methods for the synthesis thereof and synthesis intermediates.

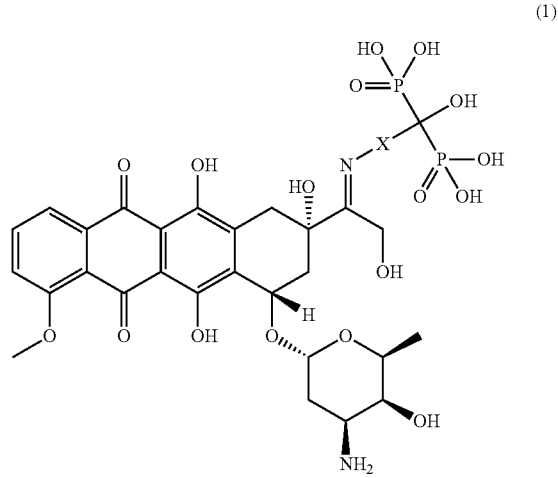

(1)

12 Claims, 2 Drawing Sheets

HYDROSOLUBLE HYDROXYBISPHOSPHONIC DERIVATIVES OF DOXORUBICIN

CROSS REFERENCE TO RELATED APPLICATIONS

The present application is a national phase entry under 35 U.S.C. § 371 of International Application No. PCT/EP2015/077279, filed Nov. 20, 2015, published in French, which claims priority from French Patent Application No. 1461253, filed Nov. 20, 2014, all of which are incorporated herein by reference.

The present invention relates to hydrosoluble hydroxybisphosphonic derivatives of doxorubicin which target bone tissue, notably for use as a medicinal product, particularly in the treatment of a bone tumor; to methods for synthesizing same; and to pharmaceutical compositions comprising such derivatives.

Bone tissue is a constantly-remodeled connective tissue composed of hydroxyapatite crystals, extracellular matrix and specialized cells (osteoblasts and osteoclasts). Any disturbance of the equilibrium between the phenomena of bone apposition and resorption induces osteolytic or osteocondensing pathologies which may be tumor-derived (with primary tumors such as osteosarcoma or secondary tumors such as bone metastases). Osteosarcomas are very aggressive bone tumors with periosteal apposition, destruction of the cortex and invasion of the soft tissues.

Osteosarcoma generally occurs in a young population (with a median age of 18 years) and represents 5% of pediatric cancers. These tumors have the particularity of establishing a vicious circle between osteolysis and tumor proliferation. The current treatment for these tumors consists of preoperative chemotherapy, followed by surgical excision of the tumor, then postoperative chemotherapy, and provides a 5-year patient survival rate of 60-70%, but of only 30% when lung metastases are detected. Faced with these rather poor survival rates, the development of novel therapies for osteosarcomas appears necessary.

Hydroxybisphosphonic (HBP) acid derivatives are molecules known for their very high affinity for bone tissue and for their property of inhibiting bone resorption (Moriceau et al., Curr Pharm Des. 2010, 16(27), 2981). Doxorubicin is one of the essential products used in the treatment of bone tumors. However, doxorubicin's toxicity greatly limits its use. The interest in chemically associating doxorubicin with an HBP is dual. Vectorization should make it possible to target the antitumor activity of doxorubicin at the bone site (and thus to treat the tumor more effectively) while decreasing the circulating concentration (thus decreasing its toxicity). At the same time, the HBP vector may improve the treatment of tumor osteolysis by its antiresorptive effect.

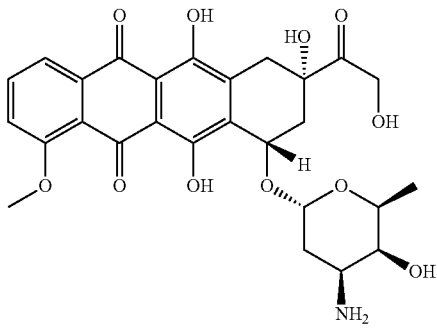

Doxorubicin

The application WO 2012/130911 notably describes this approach of chemically combining a vector with active ingredients, including doxorubicin, on a vector bearing an HBP function via an imine bond. However, the product described in the application WO 2012/130911 comprising a doxorubicin moiety (modified or not) coupled to an HBP vector proved to be insoluble (or very poorly soluble in its modified form) in water, even with organic additives (e.g., Tween®, PEG, glycerin, glucose) or with inorganic additives (e.g., sodium carbonate or bicarbonate), and in organic solvents (e.g., ethanol or dimethylsulfoxide), which makes it difficult to use this product as a medicinal product.

There is thus a need to develop novel doxorubicin derivatives coupled to an HBP vector which would be water soluble in order to allow them to be used as a medicinal product.

The present invention thus relates to a hydroxybisphosphonic derivative of doxorubicin of the following general formula (I):

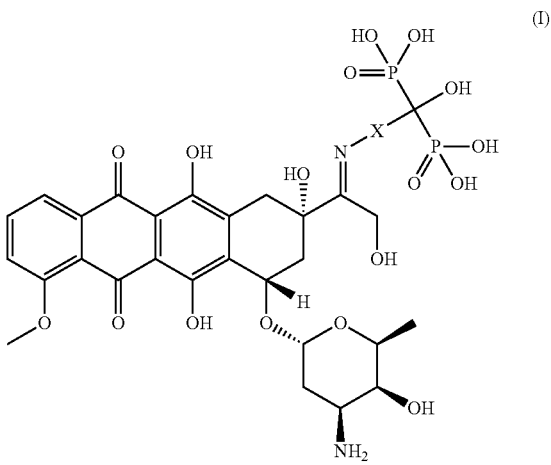

or a pharmaceutically acceptable salt thereof, wherein X represents a bivalent group selected from:

(1)

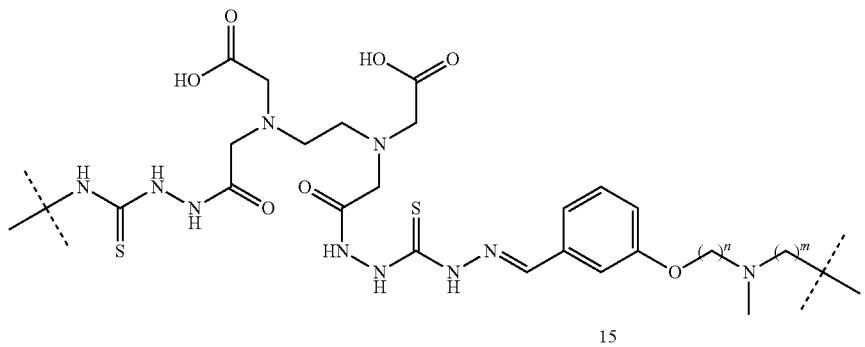

with n and m each independently representing an integer between 1 and 6, notably between 1 and 4, (2)

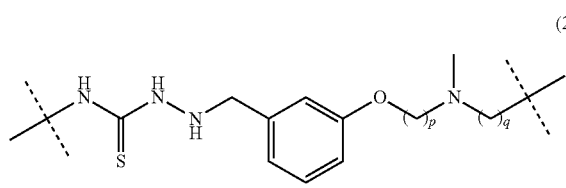

with p and q each independently representing an integer between 1 and 6, notably between 1 and 4, and (3)

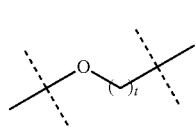

with t representing an integer between 1 and 6, notably between 1 and 4, these groups being bound to the imine function of the compound of formula (I) via their terminal nitrogen or oxygen atom and to the hydroxybisphosphonic acid function of the compound of formula (I) via their terminal carbon atom.

The compounds of formula (I) according to the present invention thus allow the vectorization of doxorubicin (antitumor agent) by a hydroxybisphosphonic vector targeting bone tissue. The way in which doxorubicin is attached and the nature of the vector are specially adapted to ensure the high solubility of the compounds in water in order to facilitate their clinical use.

In the present invention, by "pharmaceutically acceptable" is meant that which is useful in the preparation of a pharmaceutical composition that is generally safe, nontoxic and neither biologically nor otherwise undesirable and that is acceptable for veterinary as well as human pharmaceutical use.

By "pharmaceutically acceptable salt" of a compound is meant a salt that is pharmaceutically acceptable, as defined herein, and that has the desired pharmacological activity of the parent compound.

Pharmaceutically acceptable salts notably include:

(1) pharmaceutically acceptable acid addition salts formed with pharmaceutically acceptable inorganic acids such as hydrochloric acid, hydrobromic acid, sulfuric acid, nitric acid, phosphoric acid and the like; or formed with pharmaceutically acceptable organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluenesulfonic acid, trimethylacetic acid, trifluoroacetic acid and the like, and (2) pharmaceutically acceptable base addition salts formed when an acid proton present in the parent compound either is replaced by a metal ion, for example an alkaline metal ion (e.g., Na, K, Li or Cs), an alkaline-earth metal ion (e.g., Ca, Mg) or an aluminum ion; or is coordinated with a pharmaceutically acceptable organic base such as diethanolamine, ethanolamine, N-methylglucamine, triethanolamine, tromethamine and the like; or with a pharmaceutically acceptable inorganic base such as aluminum hydroxide, calcium hydroxide, potassium hydroxide, sodium carbonate, sodium bicarbonate, sodium hydroxide and the like.

Thus, n, m, p, q and t each independently represent an integer equal to 1, 2, 3, 4, 5 or 6, notably equal to 1, 2, 3 or 4.

According to a particular embodiment of the invention, n=3, m=2, p=3, q=2 and t=1. Thus, advantageously, X represents a group selected from:

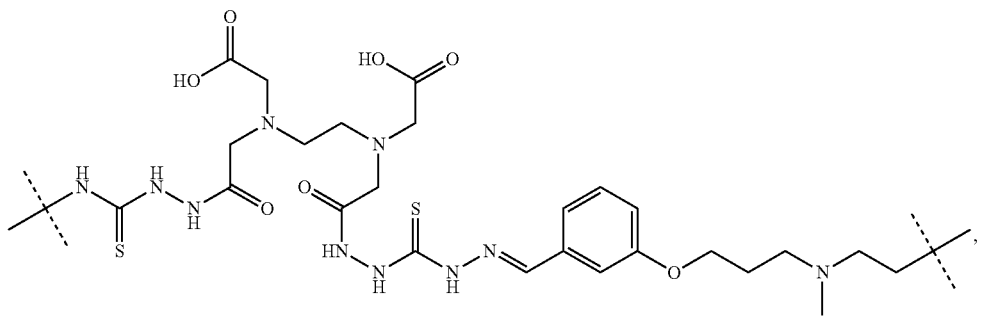

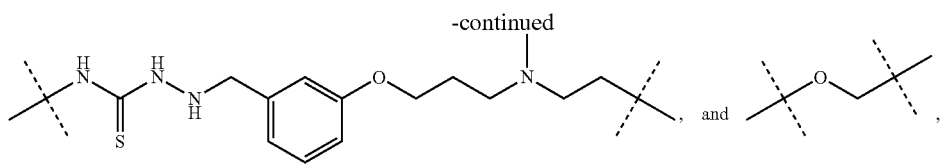

these groups being bound to the imine function of the compound of formula (I) via their terminal nitrogen or oxygen atom and to the hydroxybisphosphonic acid function of the compound of formula (I) via their terminal carbon atom.

According to a particular embodiment of the invention, the compound of formula (I) is selected from the compounds (II), (III), (IV) described in the experimental section below and pharmaceutically acceptable salts thereof.

The present invention also relates to a compound of formula (I) as described above or a pharmaceutically acceptable salt thereof, for use as a medicinal product, notably to target bone tissue.

The present invention also relates to the use of a compound of formula(I) as described above or a pharmaceutically acceptable salt thereof, to manufacture a pharmaceutical composition, targeting more particularly bone tissue.

In particular, the compounds of formula (I) according to the invention may be used to treat a bone tumor.

The present invention also relates to a method for treating a bone tumor comprising administering to a person in need thereof an effective amount of a compound of formula (I) as described above or a pharmaceutically acceptable salt thereof.

The bone tumor may be in particular a primary bone tumor such as osteosarcoma, chondrosarcoma, giant cell tumor or Ewing's sarcoma; bone metastases; or multiple myeloma.

The present invention also relates to a pharmaceutical composition comprising at least one compound of formula (I), as described above, or a pharmaceutically acceptable salt thereof and at least one pharmaceutically acceptable carrier.

This composition may be formulated so as to allow its administration, notably by parenteral route (e.g., subcutaneous, intravenous, intradermal or intramuscular), i.e., preferably in the form of an injectable solution, and intended for mammals, including humans.

The solution to be injected may be in the form of aqueous suspensions, isotonic saline solutions or sterile injectable solutions which contain pharmaceutically acceptable dispersants and/or wetting agents.

The dosing regimen will vary according to treatment and to the affection in question. The compounds of the invention as active ingredients may be in particular used at doses between 0.01 mg and 5000 mg per day, given in a single dose once per day or administered in several doses throughout the day, for example twice a day in equal doses. It may be necessary to use doses beyond these ranges, which would be obvious to the person skilled in the art.

The present invention also has as an object a pharmaceutical composition as defined above for use in the treatment of a bone tumor, notably as defined above.

The present invention also relates to methods for preparing a compound of formula (I) according to the invention.

A first method comprises the following steps:
(a) reaction of doxorubicin or a salt thereof with a compound of the following formula (A):

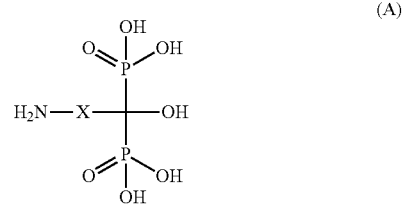

or a salt thereof,
wherein X is as defined above,
to give a compound of formula (I) according to the invention, and
(b) optionally, salification of the compound of formula (I) obtained in the preceding step (a) to give a pharmaceutically acceptable salt thereof.

Step (a):
Doxorubicin may be used in particular in the form of its hydrochloride.

The compound of formula (A) can be prepared as described in the experimental section below.

Coupling between doxorubicin or a salt thereof and the compound of formula (A) or a salt thereof may be carried out in a solvent selected from tetrahydrofuran (THF), methanol, dimethylsulfoxide (DMSO), water and mixtures thereof, notably in a water/THF mixture. This coupling may be carried out at a temperature between 0 and 80° C., in particular at room temperature.

By "room temperature" is meant, in the context of the present invention, a temperature between 15 and 40° C., preferably between 20 and 30° C., notably of about 25° C.

Step (b):
Salification of the compound of formula (I) may be carried out by reaction of the compound of formula (I) with a pharmaceutically acceptable acid or base.

A second method for preparing compounds of formula (I) for which X represents a group (1) comprises the following steps:
(i) coupling reaction of a compound of the following formula (B):

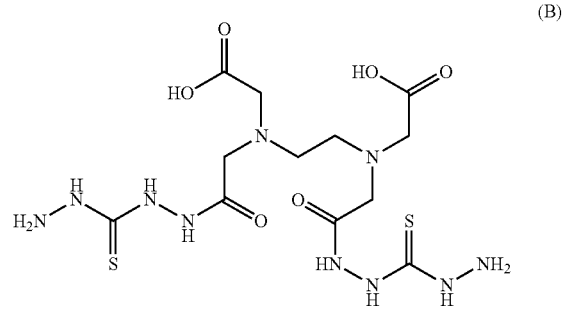 [SMILES: NNC(=S)NNC(=O)CN(CCN(CC(=O)O)CC(=O)NNC(=S)NN)CC(=O)O]

or a salt thereof, with a compound of the following formula (C):

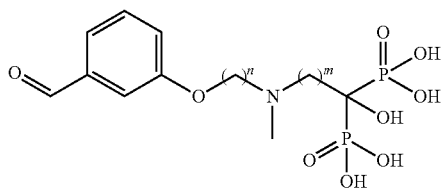

or a salt thereof,
wherein n and m are as defined above,
and doxorubicin or a salt thereof,
the coupling reaction being carried out in one step in the presence of the compound of formula (B) or a salt thereof, the compound of formula (C) or a salt thereof, and doxorubicin or a salt thereof, or in two steps by first coupling the compound of formula (B) or a salt thereof with doxorubicin or a salt thereof before carrying out the coupling with the compound of formula (C) or a salt thereof, or by first coupling the compound of formula (B) or a salt thereof with the compound of formula (C) or a salt thereof before carrying out the coupling with doxorubicin or a salt thereof,
to give a compound of formula (I) according to the invention for which X represents a group (1), and (ii) optionally, salification of the compound of formula (I) obtained in the preceding step (i) to give a pharmaceutically acceptable salt of same.

Step (i):

Doxorubicin may be used in particular in the form of its hydrochloride.

The compound of formula (B) can be prepared as described in the experimental section below by reaction of thiocarbohydrazide (compound 2) with ethylenediaminetetraacetic dianhydride (compound 1).

The compound of formula (C) can be prepared as described in the application WO 2012/130911. It may be used in particular in the form of a disodium salt.

According to a first variant, the compounds of formulas (B) and (C) and doxorubicin or a salt thereof are reacted all together to give a compound of formula (I) according to the invention for which X represents a group (1) (one-step coupling reaction).

According to a second variant (two-step coupling reaction), the compound of formula (B) or a salt thereof is reacted with doxorubicin or a salt thereof in a first step to give the intermediate compound of the following formula (D):

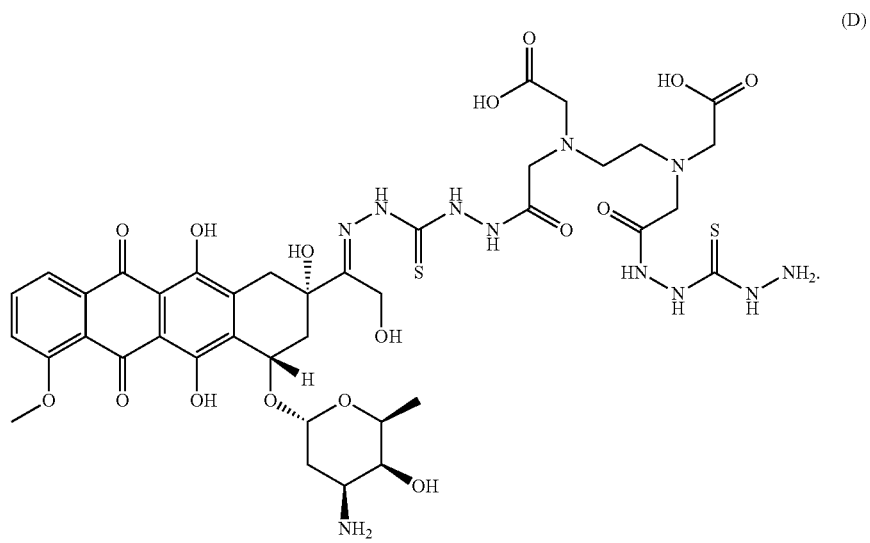 [SMILES: COc1cccc2c1C(=O)c1c(O)c3c(c(O)c1C2=O)C[C@@](O)(/C(CO)=N/NC(=S)NNC(=O)CN(CCN(CC(=O)O)CC(=O)NNC(=S)NN)CC(=O)O)C[C@@H]3O[C@H]1C[C@H](N)[C@H](O)[C@H](C)O1]

This compound of formula (D) is then reacted with the compound of formula (C) or a salt thereof in a second step to give a compound of formula (I) according to the invention for which X represents a group (1).

According to a third variant (two-step coupling reaction), the compound of formula (B) or a salt thereof is reacted with the compound of formula (C) or a salt thereof in a first step to give the intermediate compound of the following formula (E):

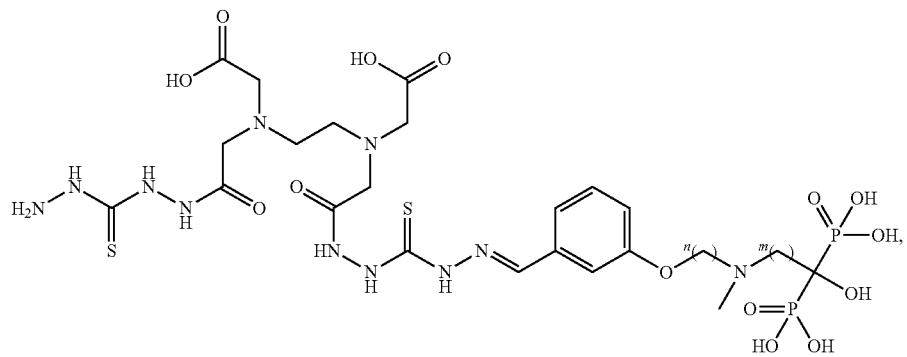
(E)

wherein n and m are as defined above.

This compound of formula (E) is then reacted with doxorubicin or a salt thereof in a second step to give a compound of formula (I) according to the invention for which X represents a group (1).

The coupling reactions mentioned above in the three variants may be carried out in acidic medium, notably in the presence of trifluoroacetic acid. A solvent selected from tetrahydrofuran, methanol, dimethylsulfoxide, water and mixtures thereof may be used, in particular a THF/water mixture. This coupling may be carried out at room temperature.

By "room temperature" is meant, in the context of the present invention, a temperature between 15 and 40° C., preferably between 20 and 30° C., notably of about 25° C.

Step (ii):

Salification of the compound of formula (I) may be carried out by reaction of the compound of formula (I) with a pharmaceutically acceptable acid or base.

The compound obtained by one of the methods described above may be separated from the reaction medium by methods well-known to the person skilled in the art, such as for example by extraction, solvent evaporation or by precipitation and filtration.

Furthermore, the compound may be purified if necessary by techniques well-known to the person skilled in the art, such as by recrystallization or precipitation if the compound is crystalline, by column chromatography (e.g., on silica gel, the silica being optionally modified notably to make it hydrophobic as on a C18 or C8 column) or by high-performance liquid chromatography (HPLC).

The present invention also has as an object a compound of formula (A) or (B) as defined above or a salt thereof, such as a pharmaceutically acceptable salt defined above.

This compound may be selected in particular from the compounds 4, 7, 13 described in the experimental section below and salts thereof, such as the pharmaceutically acceptable salts defined above.

Such compounds are useful as synthetic intermediates, in particular for preparing the compounds of formula (I) as defined above.

The present invention is illustrated by the following non-limiting examples.

FIGURES

EXAMPLES

Figure 1:
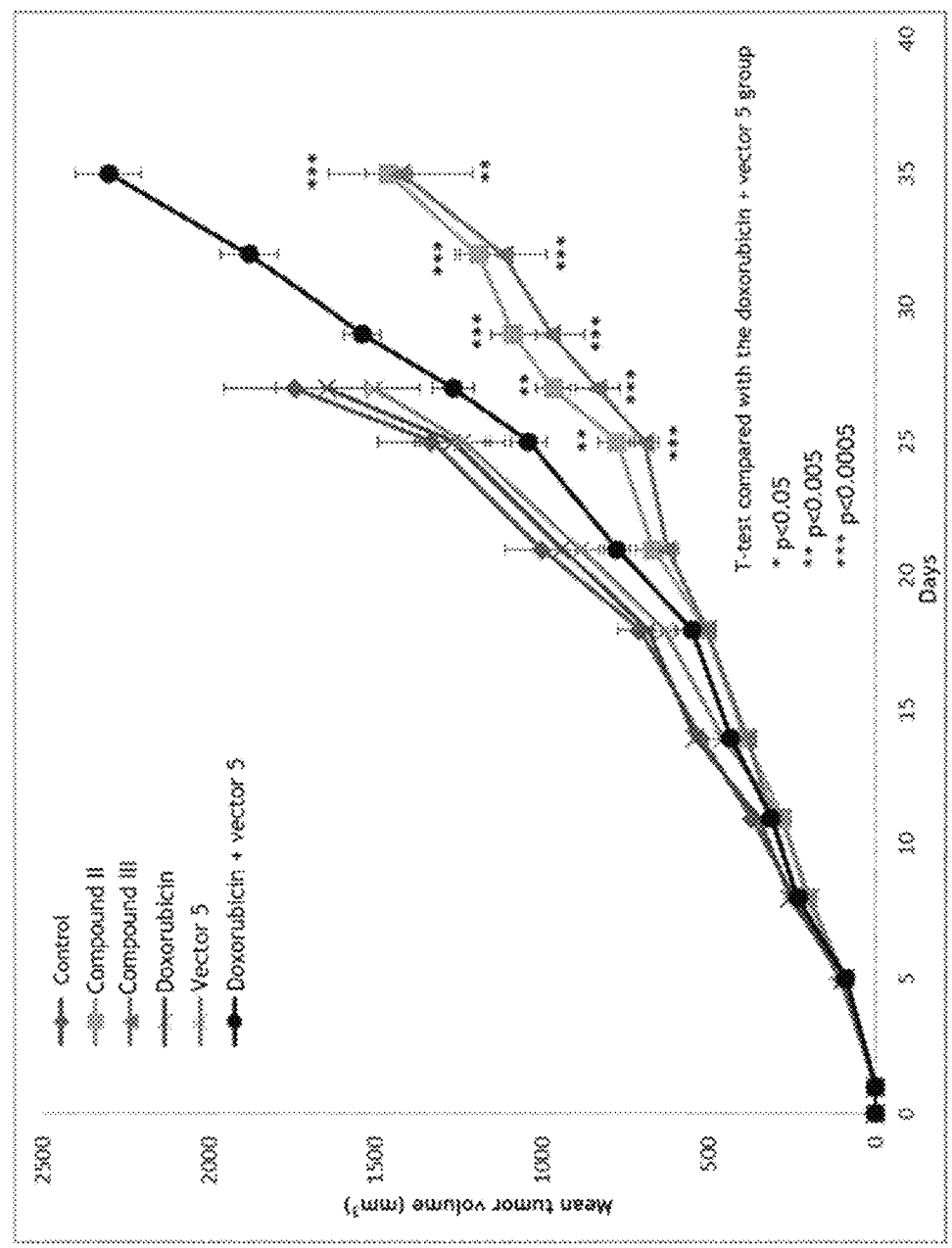
FIG. 1 represents the change over time of the mean tumor volume ($mm^3$) of an HOS tumor developed in mice in the control (CT), compound (II), compound (III), doxorubicin, vector 5, and doxorubicin+vector 5 groups.

Abbreviations used:
DMSO: Dimethylsulfoxide
DPBS: Dulbecco's Phosphate-Buffered Saline
EDTA: Ethylenediaminetetraacetic acid
ES: Electrospray
HPLC: High-performance liquid chromatography
MS: Mass spectrometer
yld: Yield
NMR: Nuclear magnetic resonance
sat: Saturated
RT: Room temperature
TFA: Trifluoroacetic acid
THF: Tetrahydrofuran
TRIS: 2-Amino-2-(hydroxymethyl)propane-1,3-diol

1. Synthesis of Compounds According to the Invention

Compound (II):

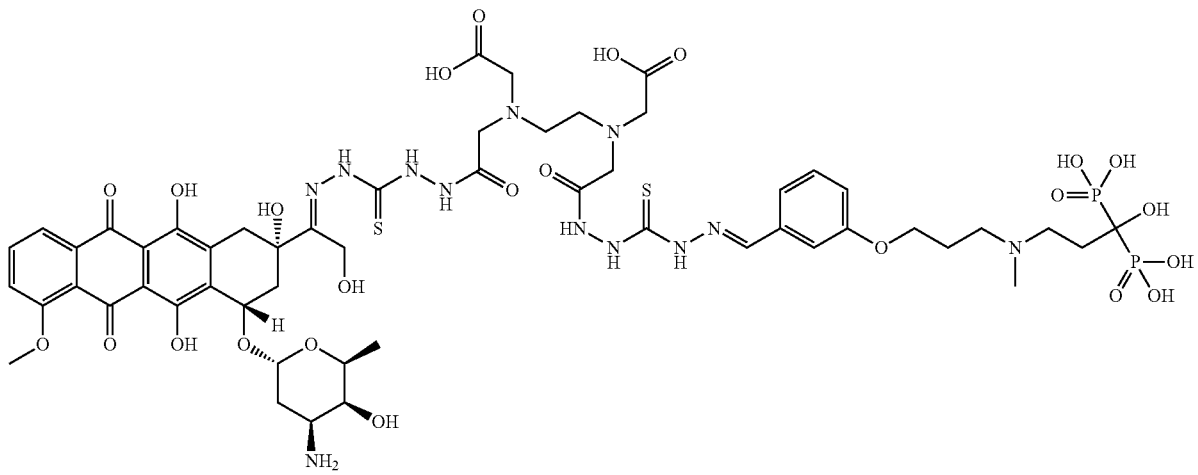 [SMILES: COc1cccc2c1C(=O)c1c(O)c3c(c(O)c1C2=O)C[C@@](O)(/C(CO)=N/NC(=S)NNC(=O)CN(CCN(CC(=O)O)CC(=O)NNC(=S)N/N=C/c1cccc(OCCCN(C)CCC(O)(P(=O)(O)O)P(=O)(O)O)c1)CC(=O)O)C[C@@H]3O[C@H]1C[C@H](N)[C@H](O)[C@H](C)O1]

Step 1:

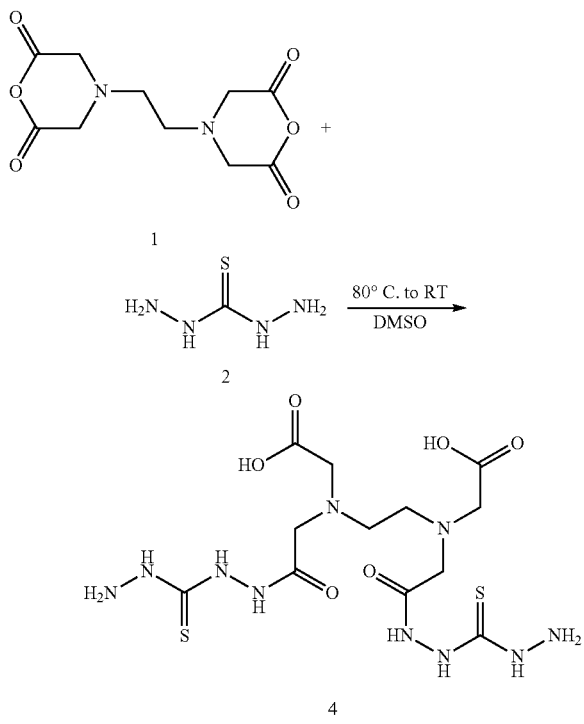

Compound 1 (3 g, 11.7 mmol) is solubilized in DMSO (15 ml) at 80° C. then is added to a solution of compound 2 (5 g, 47.2 mmol) in DMSO (30 ml) at 80° C. The transparent solution obtained is stirred 3 h at RT. The reaction mixture is diluted with a mixture of methanol (120 ml) and water (120 ml). To the transparent solution obtained, methanol (600 ml) is added with stirring followed by diethyl ether (150 ml) and stirring is continued for 5 min at RT. The precipitate obtained is filtered and washed with methanol, then solubilized completely in 150 ml of water at RT for 15 min. To the solution obtained, methanol (600 ml) is added, followed by diethyl ether (150 ml) and stirring is continued for 5 min at RT. The precipitate obtained is filtered, washed with methanol followed by diethyl ether, then dried under vacuum at RT. Compound 4 (3.2 g, yld=58%) is obtained. $^1$H NMR spectrum (D$_2$O, 400 MHz) δ, ppm: 3.87; (2H, s), 3.70; (2H, s), 3.24; (2H, s).

Step 2:

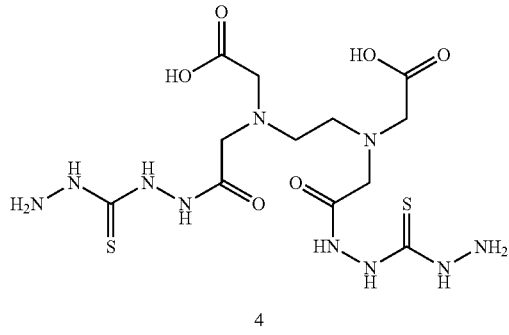

+                                    +

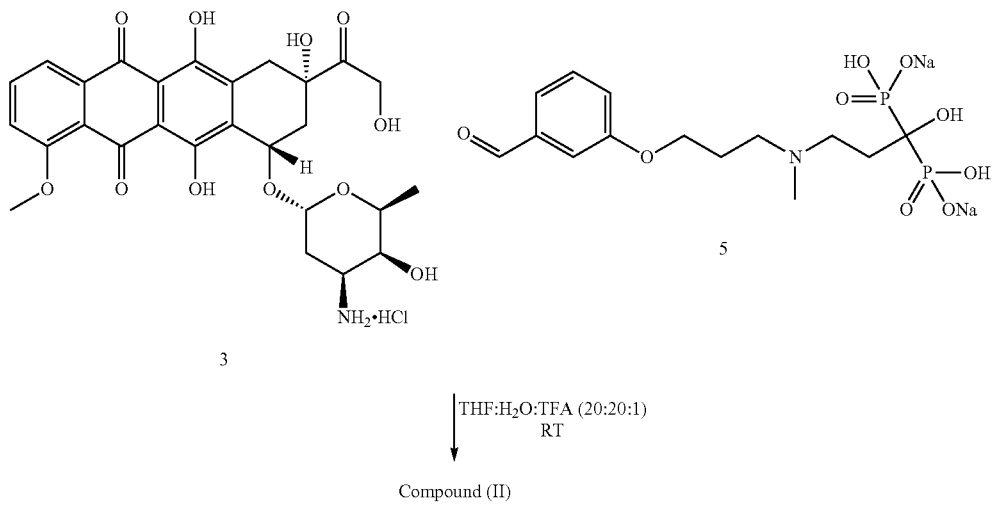

THF:H₂O:TFA (20:20:1)
RT

Compound (II)

The synthesis of compound 5 is described in the application WO 2012/130911. Under argon, a solution of compound 4 (1060 mg, 2.26 mmol) in 24 ml of a THF/H₂O/TFA (20:20:1) mixture is added all at once to a solution of compounds 3 (918 mg, 1.58 mmol) and 5 (1028 mg, 2.26 mmol) in 24 ml of the THF/H₂O/TFA (20:20:1) mixture. The dark red solution obtained is stirred at RT for 16 h protected from light. An Et₂O/MeOH (5:1) mixture (360 ml) is then added to the solution while maintaining stirring and the red precipitate suspension obtained is stirred for 5 min at RT. The precipitate is filtered and washed with Et₂O then dried under vacuum. The red powder obtained is solubilized in 10 ml of NaHCO₃sat:H₂O (1:1) mixture and the solution obtained is introduced into a C18 column then eluted with a gradient of [600 ml of 3% MeOH/H₂O+2 ml of 20% NH₃/H₂O] to [600 ml of 50% MeOH/H₂O+2 ml of 20% NH₃/H₂O]. The final product leaves starting from about 450 ml of eluent in about 150 ml of eluent. The fractions containing the final product are evaporated under vacuum to about 10 ml of solution remaining which is then diluted with MeOH (40 ml) followed by Et₂O (200 ml). The mixture obtained is stirred until a red precipitate forms, which is stirred for 5 min at RT, then filtered, washed with Et₂O, and dried under vacuum at RT. Compound (II) (526 mg, yld=23%) is obtained.

¹H NMR spectrum (1% TFA-D/DMSO-D6, 400 MHz) δ, ppm: 14.07; (1H, s), 13.36; (1H, s), 11.97; (1H, s), 11.24; (1H, s), 10.53; (1H, s), 10.48; (1H, s), 10.30; (1H, s), 9.80; (1H, s), 8.05; (1H, s), 7.95; (2H, s), 7.84; (2H, m), 7.68; (1H, dd), 7.46; (1H, s), 7.40; (1H, d), 7.33; (1H, t), 7.02; (1H, d), 5.30; (1H, s), 4.99; (1H, s), 4.61; (1H, t), 4.5-3.7; (12H, m), 3.6-2.85; (14H, m), 3.01; (1H, d), 2.81; (3H, s), 2.27; (4H, m), 2.13; (2H, m), 1.85; (1H, t), 1.65; (1H, d), 1.18; (3H, d). ³¹P NMR spectrum (1% TFA-D/DMSO-D6, 162 MHz) δ, ppm: 18.23. Mass spectrum (ES-) (m/z): [M-H]⁻1386. Purity by HPLC analysis (C18, H₂O/EDTA/NH₃-MeCN): 97%.

Compound (III):

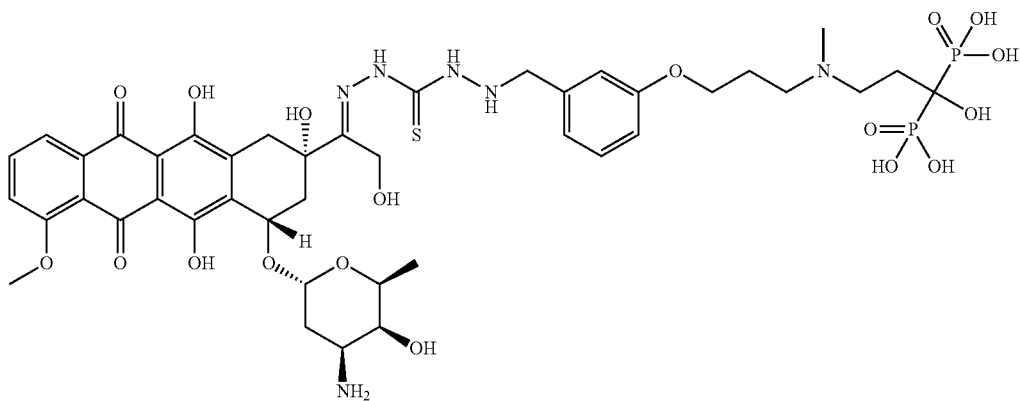 [SMILES: COc1cccc2c1C(=O)c1c(O)c3c(c(O)c1C2=O)C[C@@](O)(/C(CO)=N/NC(=S)NNCc1cccc(OCCCN(C)CCC(O)(P(=O)(O)O)P(=O)(O)O)c1)C[C@@H]3O[C@H]1C[C@H](N)[C@H](O)[C@H](C)O1]

Step 1:

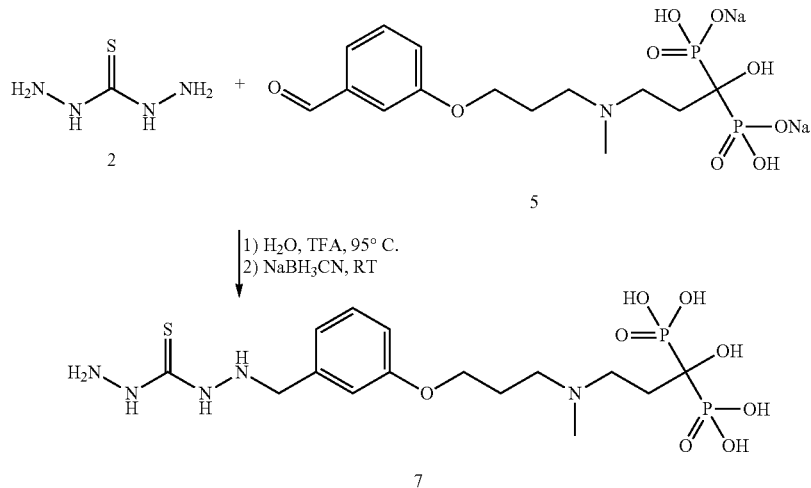

With stirring, compound 5 (1 g, 2.2 mmol) is added to a solution of compound 2 (1 g, 9.4 mmol) in water (40 ml) at 95° C. To the transparent solution obtained, TFA (0.8 ml) is added and the mixture is stirred 30 min at the same temperature. The mixture is then placed at RT and NaBH$_3$CN (0.6 g, 9.5 mmol) is added, then stirring is continued for 24 h at RT. The reaction mixture is introduced on a C18 column which is eluted with a gradient of [600 ml of 3% MeOH/H$_2$O] to [600 ml of 50% MeOH/H$_2$O]. The excess compound 2 is eluted after about 150 ml of eluent and the final product 7 is eluted after about 400 ml of eluent in a volume of about 200 ml of eluent. The fractions are evaporated under vacuum to about 10 ml of solution remaining which is then diluted by stirring with MeOH (200 ml) followed by Et$_2$O (300 ml). The precipitate obtained is filtered, washed with Et$_2$O and dried under vacuum at RT. Compound 7 (780 mg, yld=71%) is obtained.

$^1$H NMR spectrum (D20, 400 MHz) δ, ppm: 7.26; (1H, t), 6.97; (2H, m), 6.89; (1H, dd), 4.10; (2H, t), 3.89; (2H, s), 3.60-3.10; (4H, s), 2.82; (3H, s), 2.31; (2H, m), 2.19; (2H, m). $^{31}$P NMR spectrum (D$_2$O, 162 MHz) δ, ppm: 16.87. Mass spectrum (ES-) (m/z): [M-H]$^-$500.

Step 2:

The mixture of compounds 7 (250 mg, 0.5 mmol) and 3 (290 mg, 0.5 mmol) is solubilized in 6 ml of a THF/H$_2$O (1:1) mixture at 80° C., stirred at this temperature for 3 min, then evaporated to dryness under vacuum. The dried mixture obtained is left under vacuum for 5 min at 80° C. and the stoppered round-bottom flask is rapidly cooled to RT with cold water. The solid obtained is solubilized with stirring at 30-40° C. in a mixture of NaHCO$_3$sat (4 ml), water (4 ml) and THF (8 ml). The very dark transparent solution obtained is diluted with water (50 ml) and introduced on a C18 column. The column is eluted with a gradient of 600 ml of 3% MeOH/H$_2$O to 600 ml of MeOH. Compound (III) is eluted after about 400 ml of eluent in a volume of about 200 ml of eluent. The fractions are evaporated under vacuum to about 10 ml of solution remaining which is diluted by stirring with MeOH (100 ml) followed by Et$_2$O (300 ml). The red precipitate formed is filtered, washed with Et$_2$O and dried under vacuum at RT. Compound (III) (160 mg, yld=32%) is obtained.

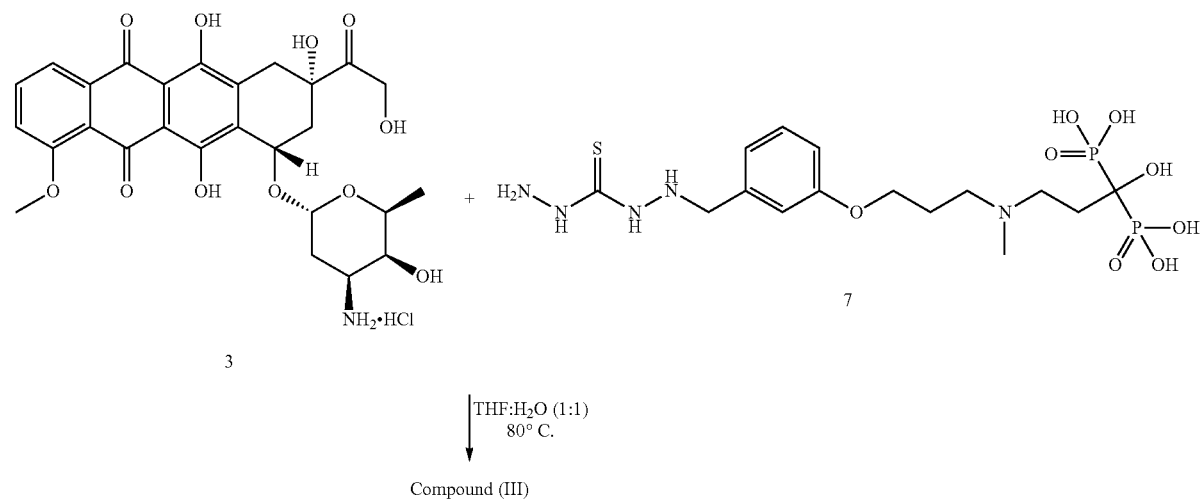

Compound (III)

¹H NMR spectrum (D₂O/THF-D8=3/1, 400 MHz) δ, ppm: 8.03; (2H, m), 7.81; (1H, d), 7.40; (1H, t), 7.21; (1H, s), 7.07; (1H, d), 5.40; (1H, s), 5.17; (1H, t), 4.42-3.99; (11H, m), 3.80-3.35; (6H, m), 3.14-3.95; (4H, m), 2.73-2.35; (7H, m), 2.22; (1H, t), 2.02; (1H, m), 1.47; (1H, m), 1.44; (3H, d).
³¹P NMR spectrum (D₂O/THF-D8=3/1, 162 MHz) δ, ppm: 14.62. Mass spectrum (ES-) (m/z): [M-H]⁻1025. Purity by HPLC analysis (C18, H₂O/EDTA/NH₃-MeCN): 98%.

Compound (IV):

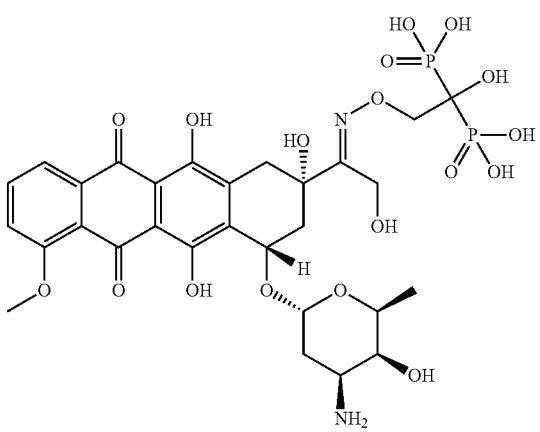 [SMILES: COc1cccc2c1C(=O)c1c(O)c3c(c(O)c1C2=O)C[C@@](O)(/C(CO)=N/OCC(O)(P(=O)(O)O)P(=O)(O)O)C[C@@H]3O[C@H]1C[C@H](N)[C@H](O)[C@H](C)O1]

Step 1:

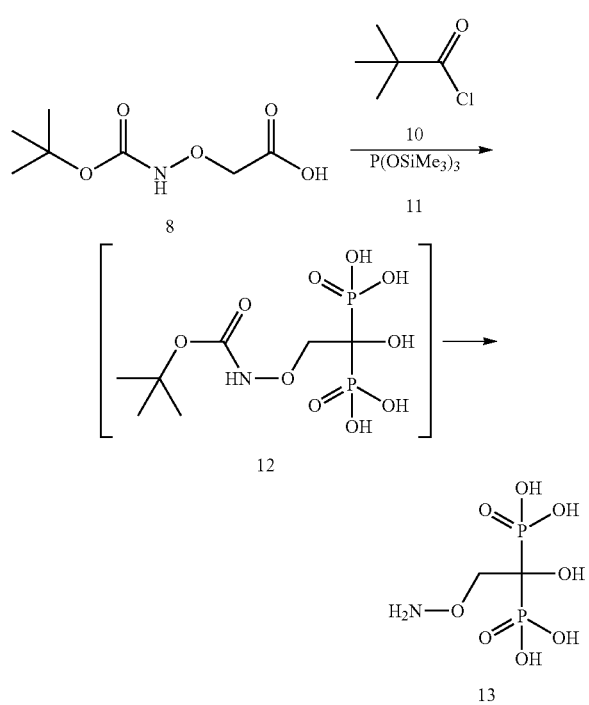

To a transparent solution of commercial product 8 (300 mg, 1.57 mmol) in THF (2 ml), triethylamine (218 µl, 1.57 mmol) is added and the homogeneous mixture is cooled to 0° C. At this temperature, the solution of product 10 (190 mg, 1.57 mmol) in THF (600 µl) is gradually added and the reaction mixture is stirred 15 min at 0° C.

The precipitate is rapidly filtered in order to collect the transparent solution under argon. To this solution, compound 11 (1.4 g, 4.71 mmol) is added and the transparent mixture obtained is stirred for 1 h at RT. Methanol (3 ml) is added and after 10 min of stirring the mixture is concentrated under vacuum to dryness at 36° C. To the residue obtained, TFA (2 ml) is added and the white precipitate formed is stirred at RT for 1 h, then the volatiles are evaporated to dryness at 36° C. The oil obtained is treated with methanol followed by ether and the white precipitate formed is filtered, washed with ether and dried. Compound 13 is obtained (205 mg, yld=55%).

¹H NMR spectrum (D₂O, 400 MHz) δ, ppm: 4.49; (2H, t).
³¹P NMR spectrum (D₂O, 162 MHz) δ, ppm: 14.18.

Step 2:

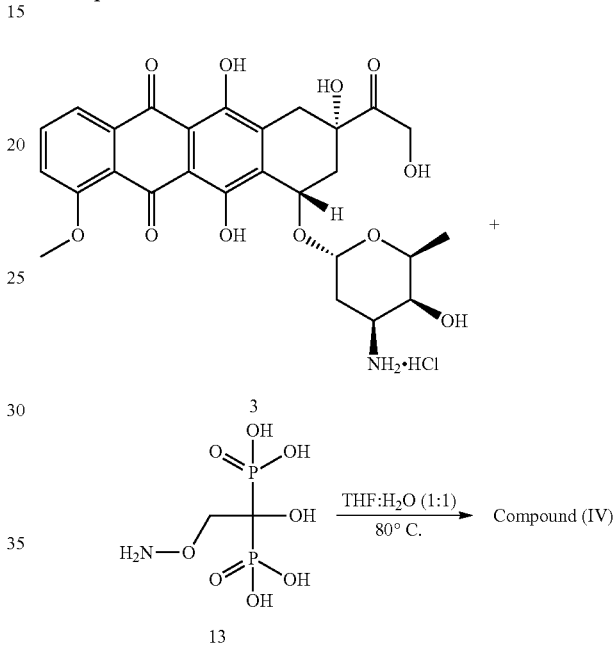

Under argon, a solution of compounds 3 (270 mg, 0.46 mmol) and 13 (100 mg, 0.42 mmol) in 3 ml of a THF/H₂O/TFA (20:20:1) mixture is stirred at RT for 16 h protected from light. 20 ml of an NaHCO₃sat:H₂O (1:1) mixture is added and the solution obtained is introduced into a C18 column then eluted with a gradient of [600 ml of 3% MeOH/H₂O+2 ml of 20% NH₃/H₂O] to [600 ml of 50% MeOH/H₂O+2 ml of 20% NH₃/H₂O]. The final product leaves starting from about 210 ml of eluent in about 150 ml of eluent. The fractions containing the final product are evaporated under vacuum to about 5 ml of solution remaining which is then diluted with methanol (40 ml) then with diethyl ether (200 ml). The mixture obtained is stirred until a red precipitate forms, which is stirred for 5 min at RT, then filtered, washed with diethyl ether, and dried under vacuum at RT. Compound (IV) (160 mg, yld=47%) is obtained.

¹H NMR spectrum (D₂O, 400 MHz) δ, ppm: 7.66; (1H, t), 7.38; (2H, m), 5.48; (1H, s), 4.84; (1H, s), 4.62; (2H, m), 4.40; (2H, s), 4.29; (1H, m), 3.90; (3H, s), 3.87; (1H, s), 3.73; (1H, t), 2.90; (1H, d), 2.57; (1H, d), 2.35; (1H, d), 2.15-1.92; (3H, m), 1.33; (3H, d).
³¹P NMR spectrum (D₂O, 162 MHz) δ, ppm: 15.19; (1P, d), 15.08; (1P, d). Mass spectrum (ES+) (m/z): [M-H]⁻807. Purity by HPLC analysis (C18, H₂O/EDTA/NH₃-MeCN): 99%.

2. Solubility of Compounds (II), (III) and (IV) Compared with Products (a) and (b).

The application WO 2012/130911 describes the derivative (b) below derived from coupling between a modified doxorubicin moiety and an HBP-type vector. This compound (b) is insoluble in water and poorly soluble in water supplemented with TRIS, which makes such a compound difficult to use.

By using the same HBP vector as in the application WO 2012/130911, the product (a) derived from the coupling of doxorubicin with this vector 5 is also insoluble in water, in water with organic additives (Tween®, PEG, glycerin, glucose, TRIS) or with inorganic additives (sodium carbonate or bicarbonate), and in organic solvents (ethanol or dimethylsulfoxide or mixtures thereof with water), which makes this product difficult to use.

|  | (II) | (III) | (IV) | (a) | (b) |
|---|---|---|---|---|---|
| 2 mg/ml solution of TRIS in water |  | not tested |  | insoluble | around 1 mM |

3. Biological Tests

Materials and Methods:

The antitumor activity of compounds (II) and (III) according to the invention was evaluated in an orthotopic, xenogeneic murine model of osteolytic osteosarcoma induced by paratibial injection of the human tumor line HOS (human osteosarcoma, ATCC) in immunosuppressed mice. The

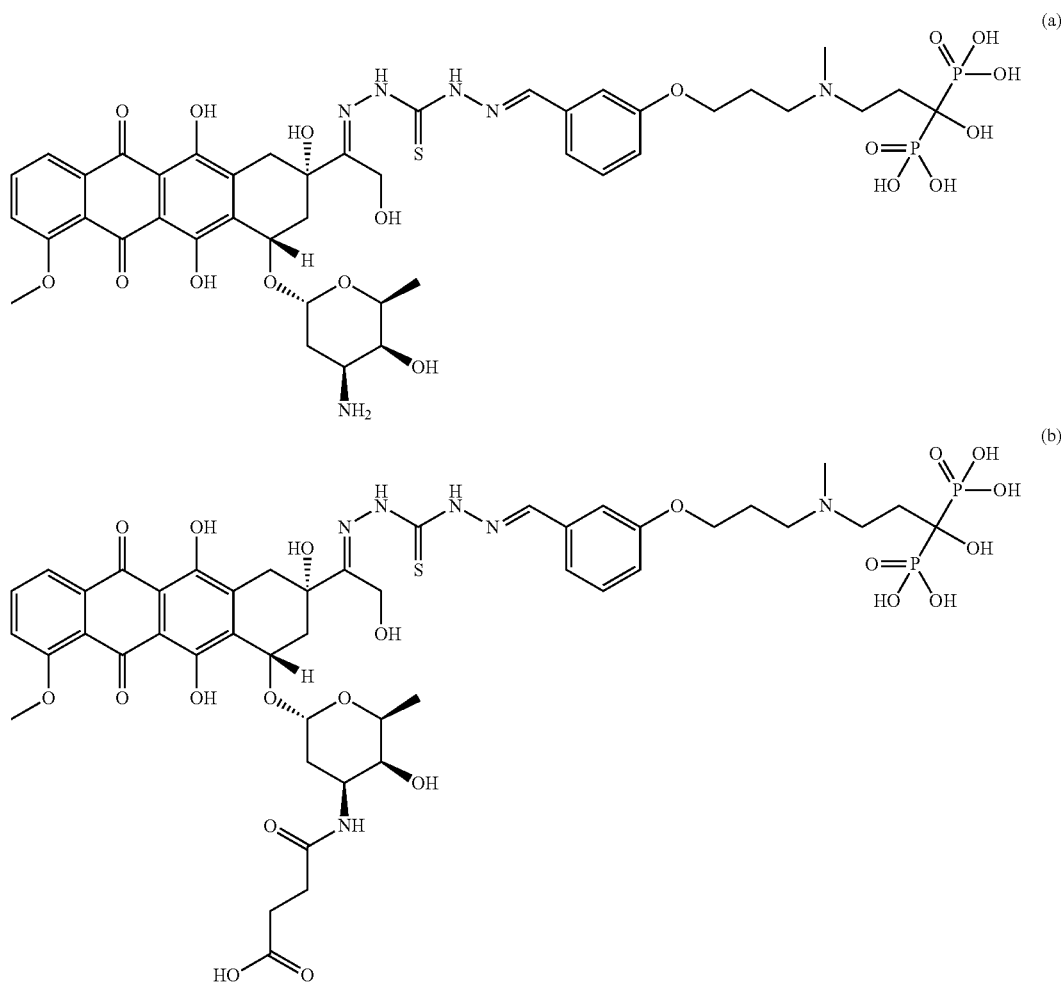

The solubility of products (II), (III) and (IV) according to the invention is greatly improved in relation to the solubility of molecules (a) and (b) (see table below), which facilitates the use of such compounds as medicinal products.

|  | (II) | (III) | (IV) | (a) | (b) |
|---|---|---|---|---|---|
| DPBS or water | around 255 mM | around 160 mM | around 315 mM | insoluble | insoluble | activity of the molecules according to the invention was compared with that of the two main subunits comprising them (doxorubicin and vector 5) alone or in combination. The treatments, on 10 animals per group, began the day following tumor induction and were administered intraperitoneally 1 to 2 times per week for 5 weeks. Tumor volumes were measured twice per week using a slide caliper and radiographic evaluation was carried out once per week. Tumor volume, expressed in $mm^3$, is calculated according to the following formula: $V=(L \times l^2)/2$ (L and l, expressed in mm, correspond to the large length and the small length of the tumor, respectively).

The following treatment groups were thus studied, each on 10 mice:

| Groups | | Treatment administered intraperitoneally. (Injection volume: 10 mL/kg) |
|---|---|---|
| 1 | Control (solvent: DPBS) | 2×/wk |
| 2 | Compound (II) (2.5 mM in DPBS) | 25 μmol/kg-2×/wk |
| 3 | Compound (III) (2.5 mM in DPBS) | 25 μmol/kg-2×/wk |
| 4 | Doxorubicin (0.37 mM in 0.9% NaCl$_{aq}$) | 3.7 μmol/kg-1×/wk |
| 5 | Vector 5 (2.5 mM in DPBS) | 25 μmol/kg-2×/wk |
| 6 | Doxorubicin (0.37 mM in 0.9% NaCl$_{aq}$) Vector 5 (2.5 mM in DPBS) | 3.7 μmol/kg-1×/wk 25 μmol/kg-2×/wk |

Results:

Toxicity. Administered at a dose of 12 mg/kg (20 μmol/kg), doxorubicin is responsible for very early weight loss in the animals (weight loss >10% requiring euthanasia of the animals after 2 weeks of treatment) and for cardiotoxicity. Compounds (II), (III) and (IV) used at a molar equivalent dose do not induce these signs of toxicity. With the aim of treating the tumor more effectively, the bifunctional molecules can even be used at higher doses than the anticancer agents alone (knowing that the typical doxorubicin treatment dose is 2 mg/kg (3.7 μmol/kg)). A study for determining the maximum usable dose thus showed similar weight loss in the mice when compounds (II), (III) and (IV) were used intravenously or intraperitoneally at a dose 13 times higher than doxorubicin alone.

Figure 2:
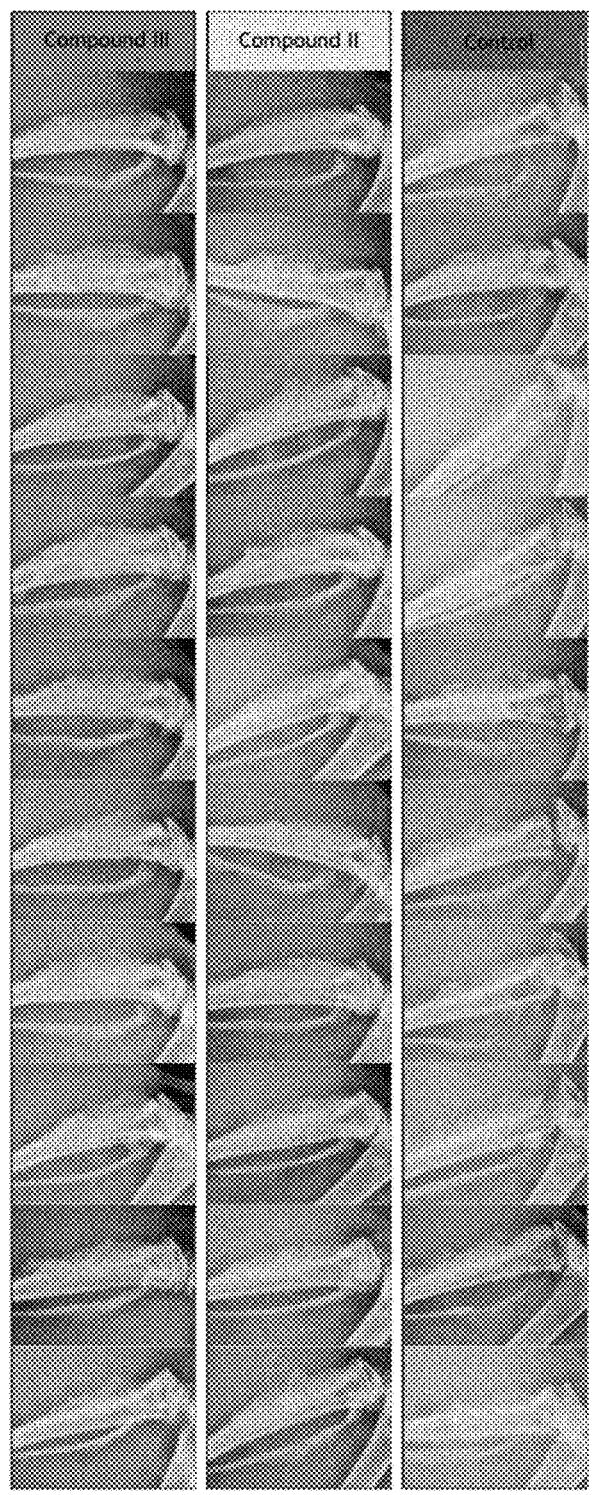
FIG. 2 represents the radiographies at Day 27 of the tumorous paws of the 10 mice of each control (CT), compound (II) and compound (III) group.

Antitumor Properties. (see FIGS. 1 and 2) Compounds (II) and (III) significantly reduce the size of extraosseous tumors measured in relation to the control group and to the groups treated with vector 5 and/or doxorubicin.

Comparison of the tumor volumes of the various groups is possible up to Day 27, however. After this date, the animals of the control, doxorubicin and vector 5 groups had to be euthanized because of excessively large tumor volumes. Moreover, at Day 32, all the animals of the doxorubicin +vector 5 group have a tumor greater than 1500 mm³ in volume whereas only one mouse from the compound (II) group exceeds this threshold.

Prevention of Bone Lesions Associated with Tumor Development. Compounds (II) and (III) reduce metaphyseal fractures, alteration of cortical integrity, and new formation of ectopic bone compared with the control, doxorubicin, vector 5, and doxorubicin +vector 5 groups. At Day 27, whereas 90% of the control group animals have fractures of the tibial metaphysis, the seat of tumor development, these fractures are not detected in any of the mice treated with compounds (II) and (III). The lesions observed in the doxorubicin group are equivalent to those of the control group (significant osteolysis on the cortex surface and metaphyseal fractures). Vector 5 (vector 5, and doxorubicin+vector 5 groups) partly reduces the metaphyseal fractures, but unfortunately large osteolytic lesions were observed on the cortical surfaces. On the other hand, the compounds according to the invention significantly prevent the osteolysis associated with tumor development in this osteosarcoma model.

The invention claimed is:

1. A compound of the following general formula (I):

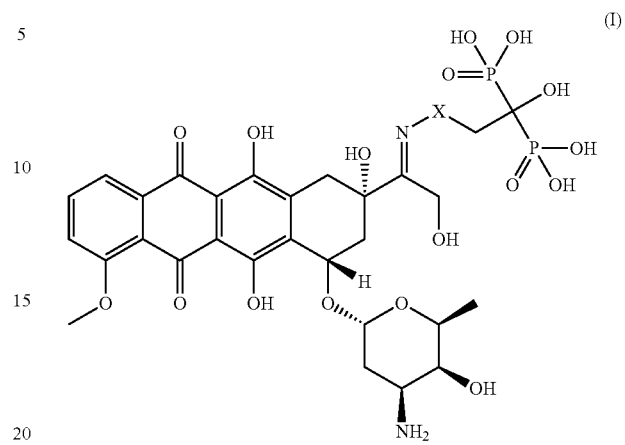

or a pharmaceutically acceptable salt thereof, wherein X represents a bivalent group selected from:

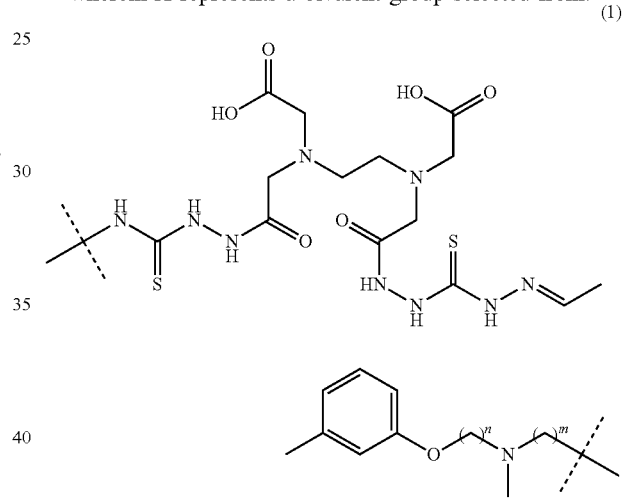

with n and m each independently representing an integer between 1 and 6,

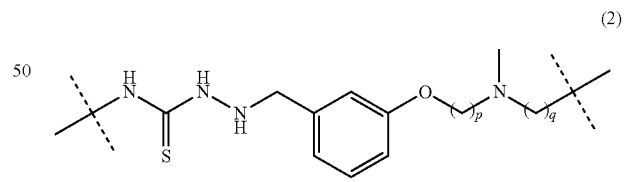

with p and q each independently representing an integer between 1 and 6, and

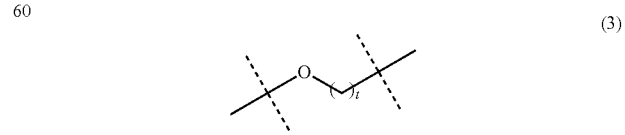

with t representing an integer between 1 and 6, these groups being bound to the imine function of the compound of formula (I) via their terminal nitrogen or oxygen atom and to the hydroxybisphosphonic acid function of the compound of formula (I) via their terminal carbon atom.

2. The compound according to claim 1, wherein n, m, p, q and t each independently represent an integer between 1 and 4.

3. The compound according to claim 1, which is selected from the following compounds:

4. A pharmaceutical composition comprising at least one compound according to claim 1 and at least one pharmaceutically acceptable carrier.

5. A method for preparing a compound according to claim 1 comprising the following steps:

(a) reaction of doxorubicin or a salt thereof with a compound of the following formula (A):

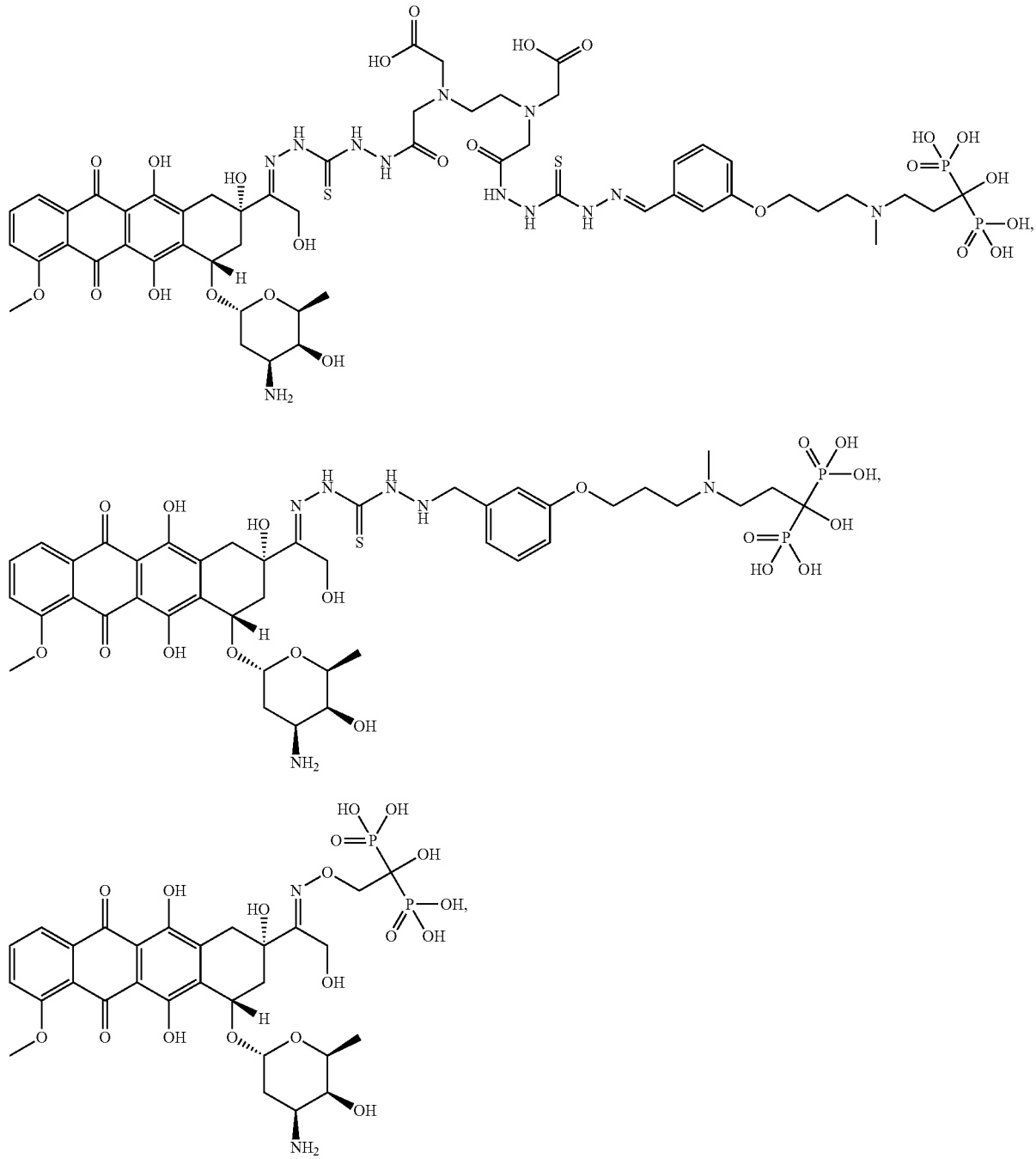

and pharmaceutically acceptable salts thereof.

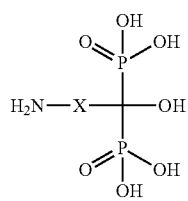

or a salt thereof,
wherein X is as defined in claim 1, to give a compound of formula (I) according to claim 1, and
(b) optionally, salification of the compound of formula (I) obtained in the preceding step (a) to give a pharmaceutically acceptable salt thereof.

6. A method for preparing a compound according to claims 1 for which X represents a group (1) comprising the following steps:
(i) coupling reaction of a compound of the following formula (B):

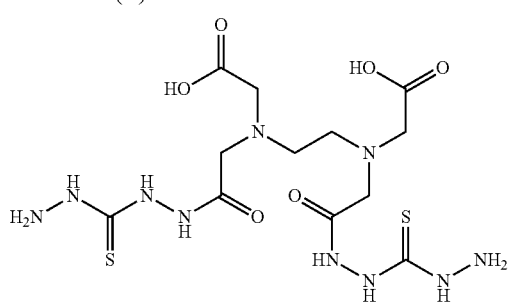

or a salt thereof,
with a compound of the following formula (C):

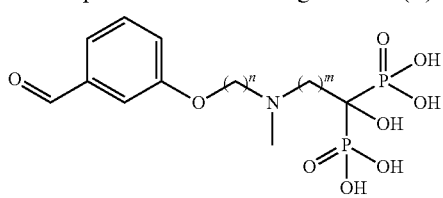

or a salt thereof, wherein n and m are as defined in claim 1,
and doxorubicin or a salt thereof,
the coupling reaction being carried out in one step in the presence of the compound of formula (B) or a salt thereof, the compound of formula (C) or a salt thereof, and doxorubicin or a salt thereof or in two steps by first coupling the compound of formula (B) or a salt thereof with doxorubicin or a salt thereof before carrying out the coupling with the compound of formula (C) or a salt thereof, or by first coupling the compound of formula (B) or a salt thereof with the compound of formula (C) or a salt thereof before carrying out the coupling with doxorubicin or a salt thereof,
to give a compound of formula (I) according to claim 1 for which X represents a group (1), and
(ii) optionally, salification of the compound of formula (I) obtained in the preceding step (i) to give a pharmaceutically acceptable salt thereof.

7. A method for treating a bone tumor comprising administering to a person in need thereof an effective amount of a compound according to claim 1.

8. The method according to claim 7, wherein the bone tumor is selected from primary bone tumors; bone metastases; and multiple myeloma.

9. The method according to claim 8, wherein the primary bone tumor is osteosarcoma, chondrosarcoma, giant cell tumor or Ewing's sarcoma.

10. A method for treating a bone tumor comprising administering to a person in need thereof an effective amount of a pharmaceutical composition according to claim 4.

11. The method according to claim 10, wherein the bone tumor is selected from primary bone tumors; bone metastases; and multiple myeloma.

12. The method according to claim 11, wherein the primary bone tumor is osteosarcoma, chondrosarcoma, giant cell tumor or Ewing's sarcoma.

* * * * *